US012661052B2

(12) United States Patent     (10) Patent No.:   US 12,661,052 B2

Hong et al.     (45) Date of Patent:    Jun. 23, 2026

(54) METHOD AND APPARATUS FOR DETERMINING POSITION OF TRANSITIONAL LEAD, AND COMPUTER DEVICE

(71) Applicant: SHENZHEN BIOCARE BIO-MEDICAL EQUIPMENT CO., LTD., Guangdong (CN)

(72) Inventors: Jiexin Hong, Guangdong (CN); Jijie Zou, Guangdong (CN); Xiaolin Yu, Guangdong (CN); Huijie Su, Guangdong (CN)

(73) Assignee: SHENZHEN BIOCARE BIO-MEDICAL EQUIPMENT CO., LTD., Guangdong (CN)

( * ) Notice: Subject to any disclaimer, the term of this patent is extended or adjusted under 35 U.S.C. 154(b) by 1112 days.

(21) Appl. No.: 17/767,445

(22) PCT Filed: Sep. 28, 2020

(86) PCT No.: PCT/CN2020/118220

§ 371 (c)(1),
(2) Date: Jul. 5, 2022

(87) PCT Pub. No.: WO2021/068778

PCT Pub. Date: Apr. 15, 2021

(65) Prior Publication Data

US 2023/0309851 A1     Oct. 5, 2023

(30) Foreign Application Priority Data

Oct. 8, 2019    (CN) .......................... 201910950633.1

(51) Int. Cl.
    *A61B 5/352*     (2021.01)
(52) U.S. Cl.
    CPC ................................... *A61B 5/352* (2021.01)

(58) Field of Classification Search
    CPC .......... A61B 5/352; A61B 5/318; A61B 5/271
        (Continued)

(56) References Cited

U.S. PATENT DOCUMENTS

| | | | |
|---|---|---|---|
| 5,792,066 A | * | 8/1998 | Kwong .................. A61B 5/349 |
| | | | 600/517 |
| 6,282,440 B1 | | 8/2001 | Brodnick et al. |
| 2003/0083587 A1 | | 5/2003 | Ferek-Petric |

FOREIGN PATENT DOCUMENTS

| | | |
|---|---|---|
| CN | 101268938 | 9/2008 |
| CN | 103908244 | 7/2014 |

(Continued)

OTHER PUBLICATIONS

Wang, Qiaoqiao et al., "The Value of Precordial Transition in the Differential Diagnosis of Ventricular Arrhythmias in the Right Ventricular Outflow Tract", Journal of Wenzhou Medical University, vol. 49, No. 3, with English abstract, Mar. 31, 2019, pp. 219-221, 225, section 1.3.

(Continued)

*Primary Examiner* — Nadia A Mahmood
(74) *Attorney, Agent, or Firm* — JCIP GLOBAL INC.

(57) ABSTRACT

Embodiments of the present invention disclose a method and an apparatus for determining a position of a transitional lead, and a computer device. The method includes: obtaining an R-wave amplitude corresponding to each of chest leads, where the chest leads include a V1 lead, a V2 lead, a V3 lead, a V4 lead, a VS lead, and a V6 lead; obtaining an S-wave amplitude corresponding to each chest lead; and determining a position of a transitional lead according to a sum of the R-wave amplitudes and the S-wave amplitudes corresponding to all the chest leads. In the foregoing manner, accuracy of determining the position of the transitional lead can be improved to a certain extent.

16 Claims, 7 Drawing Sheets

(58) Field of Classification Search
USPC ......................................................... 600/513
See application file for complete search history.

(56) References Cited

FOREIGN PATENT DOCUMENTS

| | | |
|---|---|---|
| CN | 104856669 | 8/2015 |
| CN | 105496400 | 4/2016 |
| CN | 106073760 | 11/2016 |
| CN | 106667479 | 5/2017 |
| CN | 106963361 | 7/2017 |
| CN | 109893124 | 6/2019 |
| CN | 110680305 | 1/2020 |
| JP | H02200239 | 8/1990 |
| WO | 2008007236 | 1/2008 |
| WO | 2011089488 | 7/2011 |
| WO | WO-2016170379 A1 * 10/2016 ........... A61N 1/3624 |

OTHER PUBLICATIONS

Wang, Yali, "non-official translation: # Visual Inspection of the Main Wave Direction in Twin-Lead to Determine Electrical Axis Deviation of the Heart", Harbin Medical Journal, vol. 29, No. 1, with English abstract, Feb. 25, 2009, pp. 1-4.

"International Search Report (Form PCT/ISA/210) of PCT/CN2020/118220," mailed on Dec. 17, 2020, with English translation thereof, pp. 1-6.

"Written Opinion of the International Searching Authority (Form PCT/ISA/237) of PCT/ CN2020/118220," mailed on May 29, 2018, pp. 1-5.

"Office Action of China Counterpart Application", issued on Apr. 12, 2021, p. 1-p. 10.

* cited by examiner

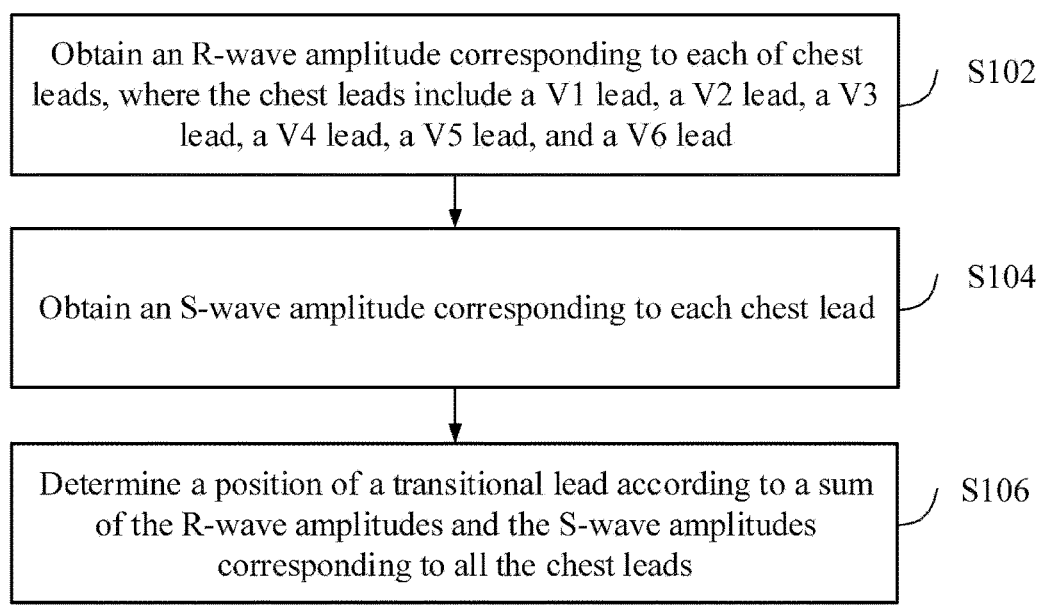

Obtain an R-wave amplitude corresponding to each of chest leads, where the chest leads include a V1 lead, a V2 lead, a V3 lead, a V4 lead, a V5 lead, and a V6 lead — S102

Obtain an S-wave amplitude corresponding to each chest lead — S104

Determine a position of a transitional lead according to a sum of the R-wave amplitudes and the S-wave amplitudes corresponding to all the chest leads — S106

FIG. 1

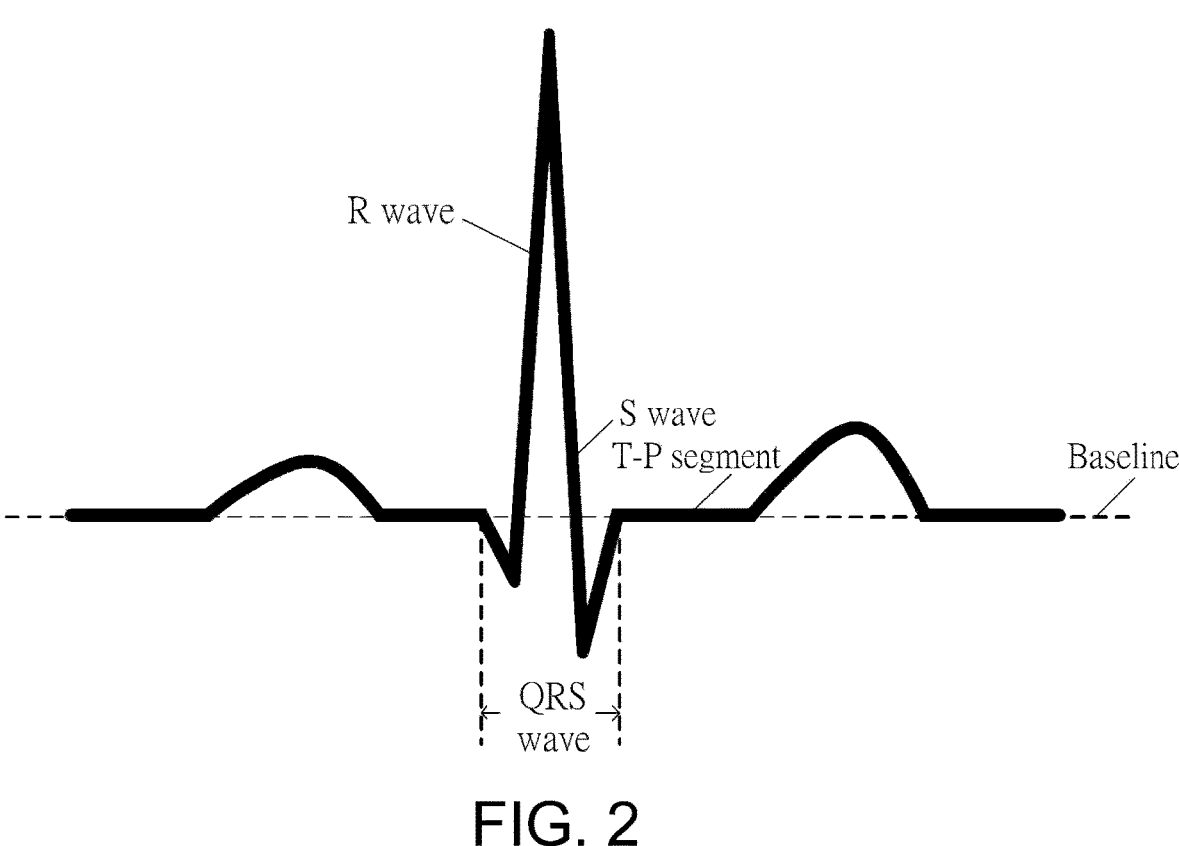

R wave

S wave
T-P segment

Baseline

QRS wave

FIG. 2

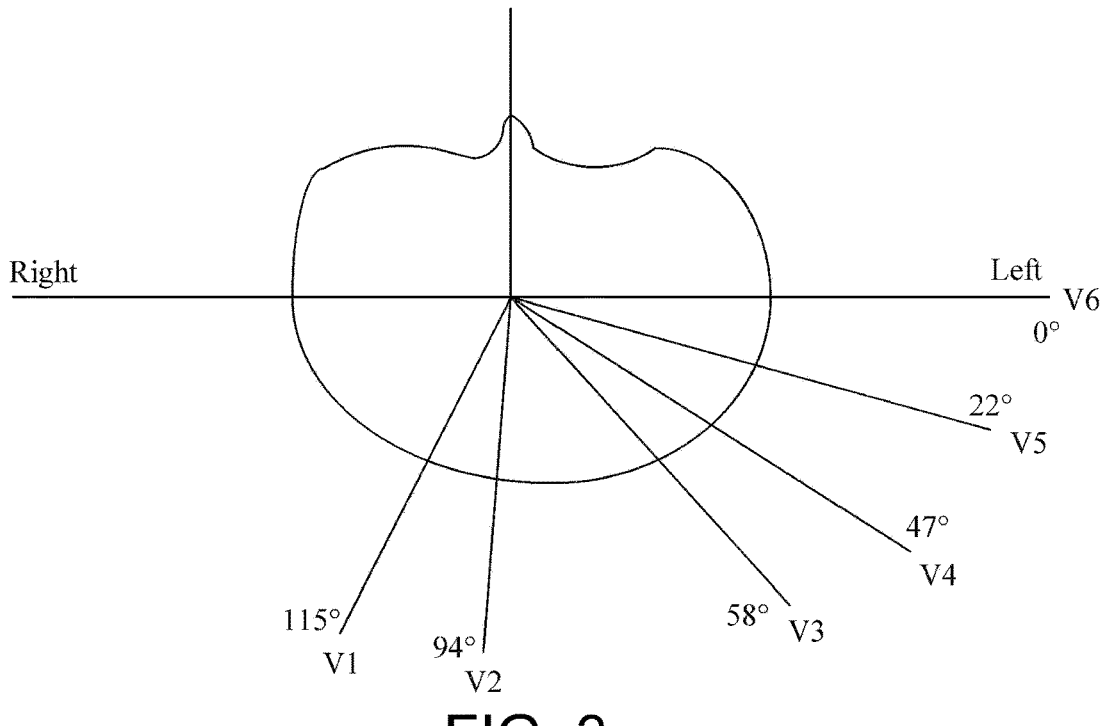
FIG. 3
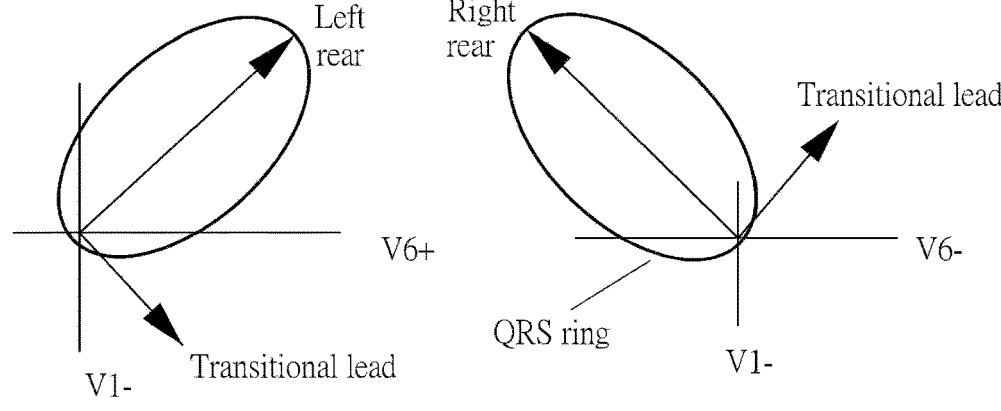
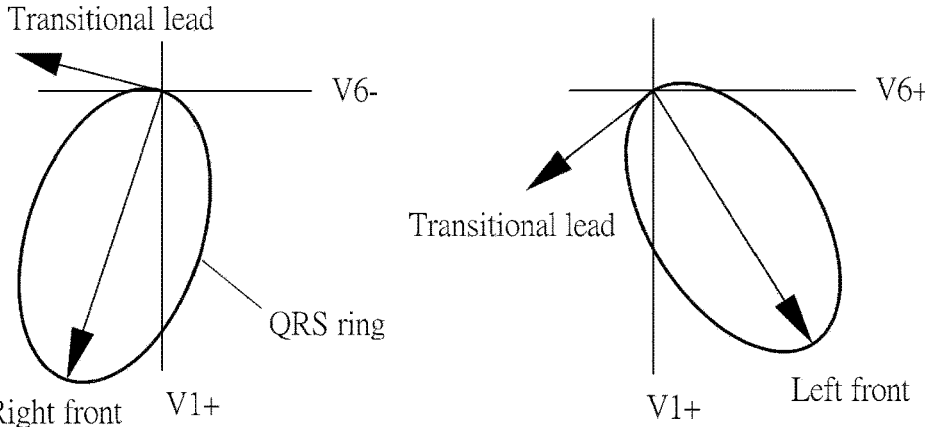
FIG. 4

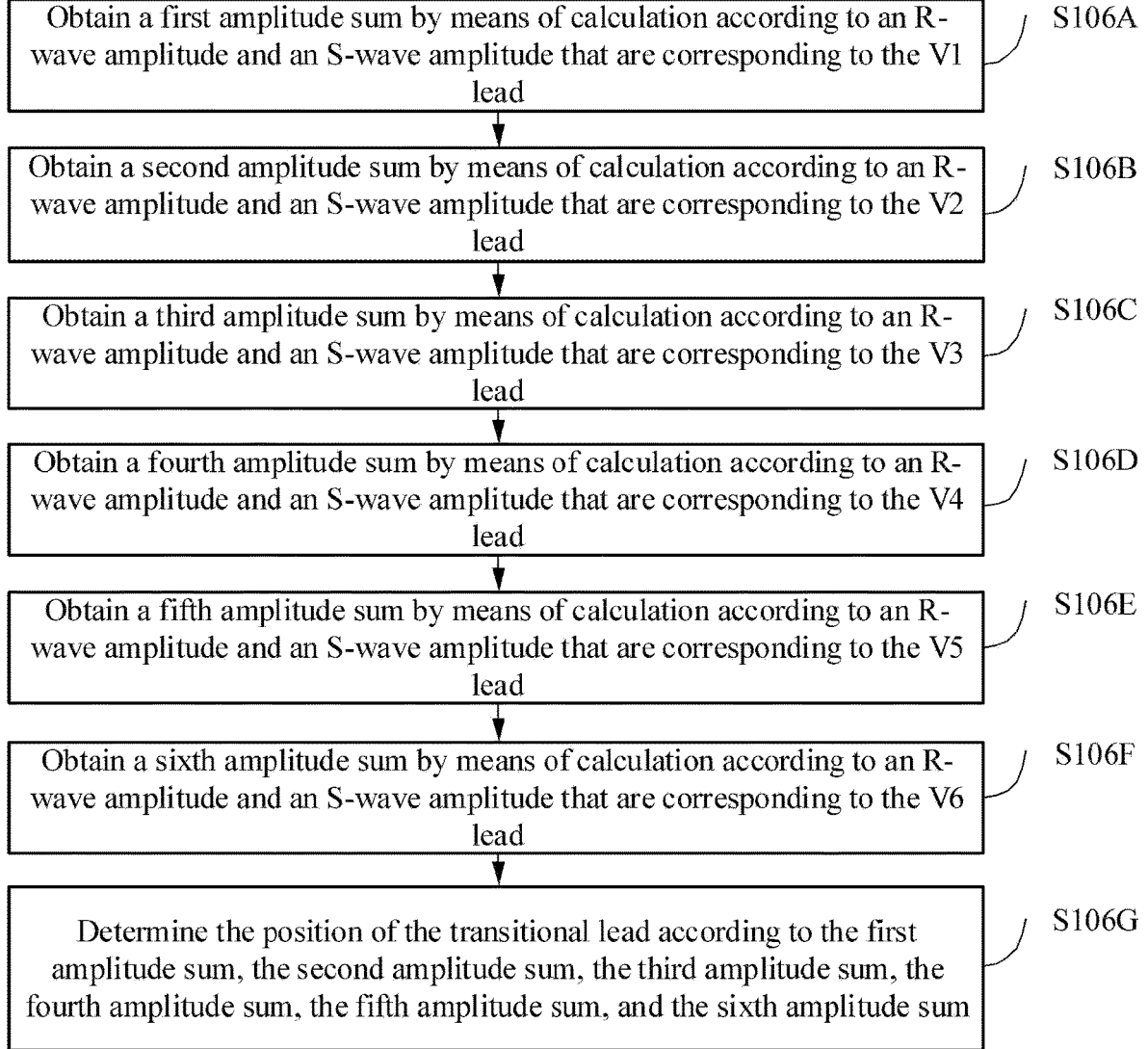

Obtain a first amplitude sum by means of calculation according to an R-wave amplitude and an S-wave amplitude that are corresponding to the V1 lead — S106A Obtain a second amplitude sum by means of calculation according to an R-wave amplitude and an S-wave amplitude that are corresponding to the V2 lead — S106B Obtain a third amplitude sum by means of calculation according to an R-wave amplitude and an S-wave amplitude that are corresponding to the V3 lead — S106C Obtain a fourth amplitude sum by means of calculation according to an R-wave amplitude and an S-wave amplitude that are corresponding to the V4 lead — S106D Obtain a fifth amplitude sum by means of calculation according to an R-wave amplitude and an S-wave amplitude that are corresponding to the V5 lead — S106E Obtain a sixth amplitude sum by means of calculation according to an R-wave amplitude and an S-wave amplitude that are corresponding to the V6 lead — S106F Determine the position of the transitional lead according to the first amplitude sum, the second amplitude sum, the third amplitude sum, the fourth amplitude sum, the fifth amplitude sum, and the sixth amplitude sum — S106G

FIG. 5

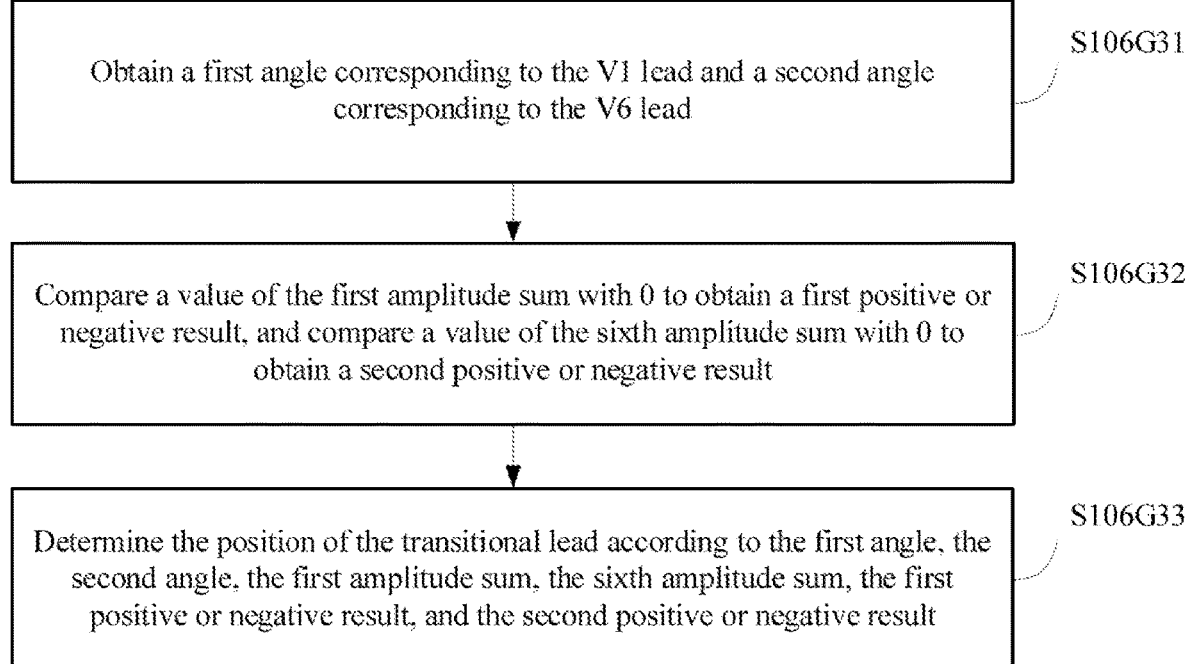

Obtain a first angle corresponding to the V1 lead and a second angle corresponding to the V6 lead

S106G31

Compare a value of the first amplitude sum with 0 to obtain a first positive or negative result, and compare a value of the sixth amplitude sum with 0 to obtain a second positive or negative result

S106G32

Determine the position of the transitional lead according to the first angle, the second angle, the first amplitude sum, the sixth amplitude sum, the first positive or negative result, and the second positive or negative result

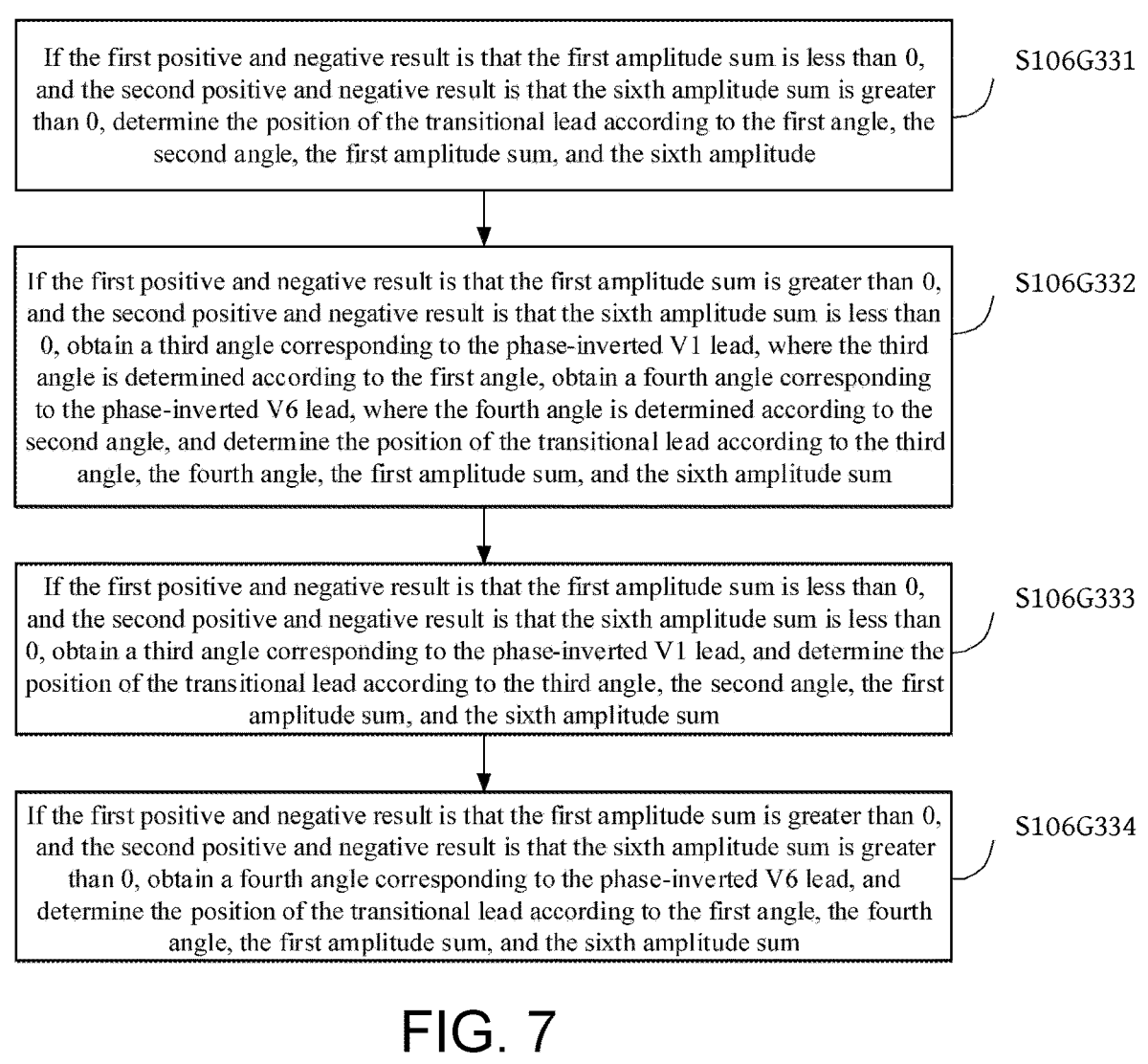

If the first positive and negative result is that the first amplitude sum is less than 0, and the second positive and negative result is that the sixth amplitude sum is greater than 0, determine the position of the transitional lead according to the first angle, the second angle, the first amplitude sum, and the sixth amplitude          S106G331

If the first positive and negative result is that the first amplitude sum is greater than 0, and the second positive and negative result is that the sixth amplitude sum is less than 0, obtain a third angle corresponding to the phase-inverted V1 lead, where the third angle is determined according to the first angle, obtain a fourth angle corresponding to the phase-inverted V6 lead, where the fourth angle is determined according to the second angle, and determine the position of the transitional lead according to the third angle, the fourth angle, the first amplitude sum, and the sixth amplitude sum          S106G332

If the first positive and negative result is that the first amplitude sum is less than 0, and the second positive and negative result is that the sixth amplitude sum is less than 0, obtain a third angle corresponding to the phase-inverted V1 lead, and determine the position of the transitional lead according to the third angle, the second angle, the first amplitude sum, and the sixth amplitude sum          S106G333

If the first positive and negative result is that the first amplitude sum is greater than 0, and the second positive and negative result is that the sixth amplitude sum is greater than 0, obtain a fourth angle corresponding to the phase-inverted V6 lead, and determine the position of the transitional lead according to the first angle, the fourth angle, the first amplitude sum, and the sixth amplitude sum          S106G334

FIG. 7

METHOD AND APPARATUS FOR DETERMINING POSITION OF TRANSITIONAL LEAD, AND COMPUTER DEVICE

CROSS-REFERENCE TO RELATED APPLICATION

This application is a 371 of international application of PCT application serial no. PCT/CN2020/118220, filed on Sep. 28, 2020, which claims the priority benefit of China application no. 201910950633.1, filed on Oct. 8, 2019. The entirety of each of the above mentioned patent applications is hereby incorporated by reference herein and made a part of this specification.

TECHNICAL FIELD

This application relates to the field of electrocardio technologies, and in particular, to a method and an apparatus for determining a position of a transitional lead, and a computer device.

BACKGROUND

In the field of electrocardio diagnosis, a position of a transitional lead is an important indicator of preoperative positioning of arrhythmia. An existing method is mainly as follows: First, a ratio of an R-wave amplitude to an S-wave amplitude of each chest lead is calculated, and then a position of a chest lead corresponding to a ratio 1 is determined as a position of a transitional lead shaft. If the ratio of the R-wave amplitude to the S-wave amplitude of each chest lead is not 1, a position of a chest lead whose ratio is the closest to 1 is determined as the position of the transitional lead shaft, thereby implementing positioning of the transitional lead shaft.

It can be learned that the foregoing method for determining the position of the transitional lead shaft by using the ratio of the R wave to the S wave is not accurate.

SUMMARY

Based on this, for the foregoing problem, a method and an apparatus for determining a position of a transitional lead with high accuracy and a computer device need to be proposed.

A method for determining a position of a transitional lead includes:

obtaining an R-wave amplitude corresponding to each of chest leads, where the chest leads include a V1 lead, a V2 lead, a V3 lead, a V4 lead, a V5 lead, and a V6 lead;

obtaining an S-wave amplitude corresponding to each chest lead; and determining a position of a transitional lead according to a sum of the R-wave amplitudes and the S-wave amplitudes corresponding to all the chest leads.

In an embodiment, the determining a position of a transitional lead according to a sum of the R-wave amplitudes and the S-wave amplitudes corresponding to all the chest leads includes: obtaining a first amplitude sum by means of calculation according to an R-wave amplitude and an S-wave amplitude that are corresponding to the V1 lead; obtaining a second amplitude sum by means of calculation according to an R-wave amplitude and an S-wave amplitude that are corresponding to the V2 lead; obtaining a third amplitude sum by means of calculation according to an R-wave amplitude and an S-wave amplitude that are corresponding to the V3 lead; obtaining a fourth amplitude sum by means of calculation according to an R-wave amplitude and an S-wave amplitude that are corresponding to the V4 lead; obtaining a fifth amplitude sum by means of calculation according to an R-wave amplitude and an S-wave amplitude that are corresponding to the V5 lead; obtaining a sixth amplitude sum by means of calculation according to an R-wave amplitude and an S-wave amplitude that are corresponding to the V6 lead; and determining the position of the transitional lead according to the first amplitude sum, the second amplitude sum, the third amplitude sum, the fourth amplitude sum, the fifth amplitude sum, and the sixth amplitude sum.

In an embodiment, the determining the position of the transitional lead according to the first amplitude sum, the second amplitude sum, the third amplitude sum, the fourth amplitude sum, the fifth amplitude sum, and the sixth amplitude sum includes: if the first amplitude sum, the second amplitude sum, the third amplitude sum, the fourth amplitude sum, the fifth amplitude sum, and the sixth amplitude sum include an amplitude sum whose value is 0, determining a target lead corresponding to the amplitude sum whose value is 0; and determining a position corresponding to the target lead as the position of the transitional lead.

In an embodiment, the determining the position of the transitional lead according to the first amplitude sum, the second amplitude sum, the third amplitude sum, the fourth amplitude sum, the fifth amplitude sum, and the sixth amplitude sum includes: if the first amplitude sum, the second amplitude sum, the third amplitude sum, the fourth amplitude sum, the fifth amplitude sum, and the sixth amplitude sum do not include an amplitude sum whose value is 0, determining the position of the transitional lead according to the first amplitude sum and the sixth amplitude sum.

In an embodiment, the determining the position of the transitional lead according to the first amplitude sum and the sixth amplitude sum includes: obtaining a first angle corresponding to the V1 lead and a second angle corresponding to the V6 lead; comparing a value of the first amplitude sum with 0 to obtain a first positive or negative result, and comparing a value of the sixth amplitude sum with 0 to obtain a second positive or negative result; and determining the position of the transitional lead according to the first angle, the second angle, the first amplitude sum, the sixth amplitude sum, the first positive or negative result, and the second positive or negative result.

In an embodiment, the determining the position of the transitional lead according to the first angle, the second angle, the first amplitude sum, the sixth amplitude sum, the first positive or negative result, and the second positive or negative result includes: if the first positive or negative result is that the first amplitude sum is less than 0, and the second positive or negative result is that the sixth amplitude sum is greater than 0, determining the position of the transitional lead according to the first angle, the second angle, the first amplitude sum, and the sixth amplitude; or if the first positive or negative result is that the first amplitude sum is greater than 0, and the second positive or negative result is that the sixth amplitude sum is less than 0, obtaining a third angle corresponding to the phase-inverted V1 lead, where the third angle is determined according to the first angle, obtaining a fourth angle corresponding to the phase-inverted V6 lead, where the fourth angle is determined according to the second angle, and determining the position of the transitional lead according to the third angle, the fourth angle, the first amplitude sum, and the sixth amplitude sum; or if the first positive or negative result is that the first amplitude sum is less than 0, and the second positive or negative result is that the sixth amplitude sum is less than 0, obtaining a third angle corresponding to the phase-inverted V1 lead, and determining the position of the transitional lead according to the third angle, the second angle, the first amplitude sum, and the sixth amplitude sum; or if the first positive or negative result is that the first amplitude sum is greater than 0, and the second positive or negative result is that the sixth amplitude sum is greater than 0, obtaining a fourth angle corresponding to the phase-inverted V6 lead, and determining the position of the transitional lead according to the first angle, the fourth angle, the first amplitude sum, and the sixth amplitude sum.

An apparatus for determining a position of a transitional lead includes:

a first obtaining module, configured to obtain an R-wave amplitude corresponding to each of chest leads, where the chest leads include a V1 lead, a V2 lead, a V3 lead, a V4 lead, a V5 lead, and a V6 lead;

a second obtaining module, configured to obtain an S-wave amplitude corresponding to each chest lead; and a position determining module, configured to determine a position of a transitional lead according to a sum of the R-wave amplitudes and the S-wave amplitudes corresponding to all the chest leads.

In an embodiment, the position determining module includes: a first amplitude module, configured to obtain a first amplitude sum by means of calculation according to an R-wave amplitude and an S-wave amplitude that are corresponding to the V1 lead; a second amplitude module, configured to obtain a second amplitude sum by means of calculation according to an R-wave amplitude and an S-wave amplitude that are corresponding to the V2 lead; a third amplitude module, configured to obtain a third amplitude sum by means of calculation according to an R-wave amplitude and an S-wave amplitude that are corresponding to the V3 lead; a fourth amplitude module, configured to obtain a fourth amplitude sum by means of calculation according to an R-wave amplitude and an S-wave amplitude that are corresponding to the V4 lead; a fifth amplitude module, configured to obtain a fifth amplitude sum by means of calculation according to an R-wave amplitude and an S-wave amplitude that are corresponding to the V5 lead; a sixth amplitude module, configured to obtain a sixth amplitude sum by means of calculation according to an R-wave amplitude and an S-wave amplitude that are corresponding to the V6 lead; and an amplitude synthesis module, configured to determine the position of the transitional lead according to the first amplitude sum, the second amplitude sum, the third amplitude sum, the fourth amplitude sum, the fifth amplitude sum, and the sixth amplitude sum.

In an embodiment, the amplitude synthesis module includes: a 0-value amplitude module, configured to: if the first amplitude sum, the second amplitude sum, the third amplitude sum, the fourth amplitude sum, the fifth amplitude sum, and the sixth amplitude sum include an amplitude sum whose value is 0, determine a target lead corresponding to the amplitude sum whose value is 0; and a 0-value position module, configured to determine a position corresponding to the target lead as the position of the transitional lead.

In an embodiment, the amplitude synthesis module includes a non-0-value amplitude module configured to: if the first amplitude sum, the second amplitude sum, the third amplitude sum, the fourth amplitude sum, the fifth amplitude sum, and the sixth amplitude sum do not include an amplitude sum whose value is 0, determine the position of the transitional lead according to the first amplitude sum and the sixth amplitude sum.

In an embodiment, the non-0-value amplitude module includes: a first angle module, configured to obtain a first angle corresponding to the V1 lead and a second angle corresponding to the V6 lead; a second angle module, configured to compare a value of the first amplitude sum with 0 to obtain a first positive or negative result, and compare a value of the sixth amplitude sum with 0 to obtain a second positive or negative result; and an angle position module, configured to determine the position of the transitional lead according to the first angle, the second angle, the first amplitude sum, the sixth amplitude sum, the first positive or negative result, and the second positive or negative result.

In an embodiment, the angle position module includes: a first angle position module, configured to: if the first positive or negative result is that the first amplitude sum is less than 0, and the second positive or negative result is that the sixth amplitude sum is greater than 0, determine the position of the transitional lead according to the first angle, the second angle, the first amplitude sum, and the sixth amplitude; a second angle position module, configured to: if the first positive or negative result is that the first amplitude sum is greater than 0, and the second positive or negative result is that the sixth amplitude sum is less than 0, obtain a third angle corresponding to the phase-inverted V1 lead, where the third angle is determined according to the first angle, obtain a fourth angle corresponding to the phase-inverted V6 lead, where the fourth angle is determined according to the second angle, and determine the position of the transitional lead according to the third angle, the fourth angle, the first amplitude sum, and the sixth amplitude sum; a third angle position module, configured to: if the first positive or negative result is that the first amplitude sum is less than 0, and the second positive or negative result is that the sixth amplitude sum is less than 0, obtain a third angle corresponding to the phase-inverted V1 lead, and determine the position of the transitional lead according to the third angle, the second angle, the first amplitude sum, and the sixth amplitude sum; and a fourth angle position module, configured to: if the first positive or negative result is that the first amplitude sum is greater than 0, and the second positive or negative result is that the sixth amplitude sum is greater than 0, obtain a fourth angle corresponding to the phase-inverted V6 lead, and determine the position of the transitional lead according to the first angle, the fourth angle, the first amplitude sum, and the sixth amplitude sum.

A computer device includes a memory and a processor, where the memory stores a computer program, and when the computer program is executed by the processor, the processor performs the following steps:

obtaining an R-wave amplitude corresponding to each of chest leads, where the chest leads include a V1 lead, a V2 lead, a V3 lead, a V4 lead, a V5 lead, and a V6 lead;

obtaining an S-wave amplitude corresponding to each chest lead; and determining a position of a transitional lead according to a sum of the R-wave amplitudes and the S-wave amplitudes corresponding to all the chest leads.

A computer readable storage medium stores a computer program, and when the computer program is executed by a processor, the processor performs the following steps:

obtaining an R-wave amplitude corresponding to each of chest leads, where the chest leads include a V1 lead, a V2 lead, a V3 lead, a V4 lead, a V5 lead, and a V6 lead;

obtaining an S-wave amplitude corresponding to each chest lead; and determining a position of a transitional lead according to a sum of the R-wave amplitudes and the S-wave amplitudes corresponding to all the chest leads.

Implementing the embodiments of the present invention has the following beneficial effects:

The present invention provides a method and an apparatus for determining a position of a transitional lead, and a computer device. The method includes: first obtaining an R-wave amplitude corresponding to each of chest leads, where the chest leads include a V1 lead, a V2 lead, a V3 lead, a V4 lead, a V5 lead, and a V6 lead; then obtaining an S-wave amplitude corresponding to each chest lead; and finally determining a position of a transitional lead according to a sum of the R-wave amplitudes and the S-wave amplitudes corresponding to all the chest leads. It can be learned that, in the foregoing manner, compared with a manner in which a target lead shaft is determined by using a ratio of an R wave to an S wave, and then a position of the target lead shaft is determined as a position of a transitional lead shaft, this manner is capable of directly determining the position of the transitional lead, and has higher accuracy.

BRIEF DESCRIPTION OF THE DRAWINGS

To describe the technical solutions in the embodiments of the present invention or in the prior art more clearly, the following briefly describes the accompanying drawings required for describing the embodiments or the prior art. Clearly, the accompanying drawings in the following description show merely some embodiments of the present invention, and a person of ordinary skill in the art may still derive other drawings from these accompanying drawings without creative efforts.

FIG. 1 is a schematic flowchart of implementation of a method for determining a position of a transitional lead according to an embodiment;

FIG. 2 is a schematic diagram of an electrocardio wave amplitude according to an embodiment;

FIG. 3 is a schematic diagram of orientations of leads on a transverse plane according to an embodiment;

FIG. 4 is a schematic diagram of a position of a transitional lead and a position of a lead according to an embodiment;

FIG. 5 is a schematic flowchart of implementation of step 106 according to an embodiment;

FIG. 6 is a schematic flowchart of implementation of step 106G3 according to an embodiment;

FIG. 7 is a schematic flowchart of implementation of step 106G33 according to an embodiment;

DESCRIPTION OF THE EMBODIMENTS

Figure 8:
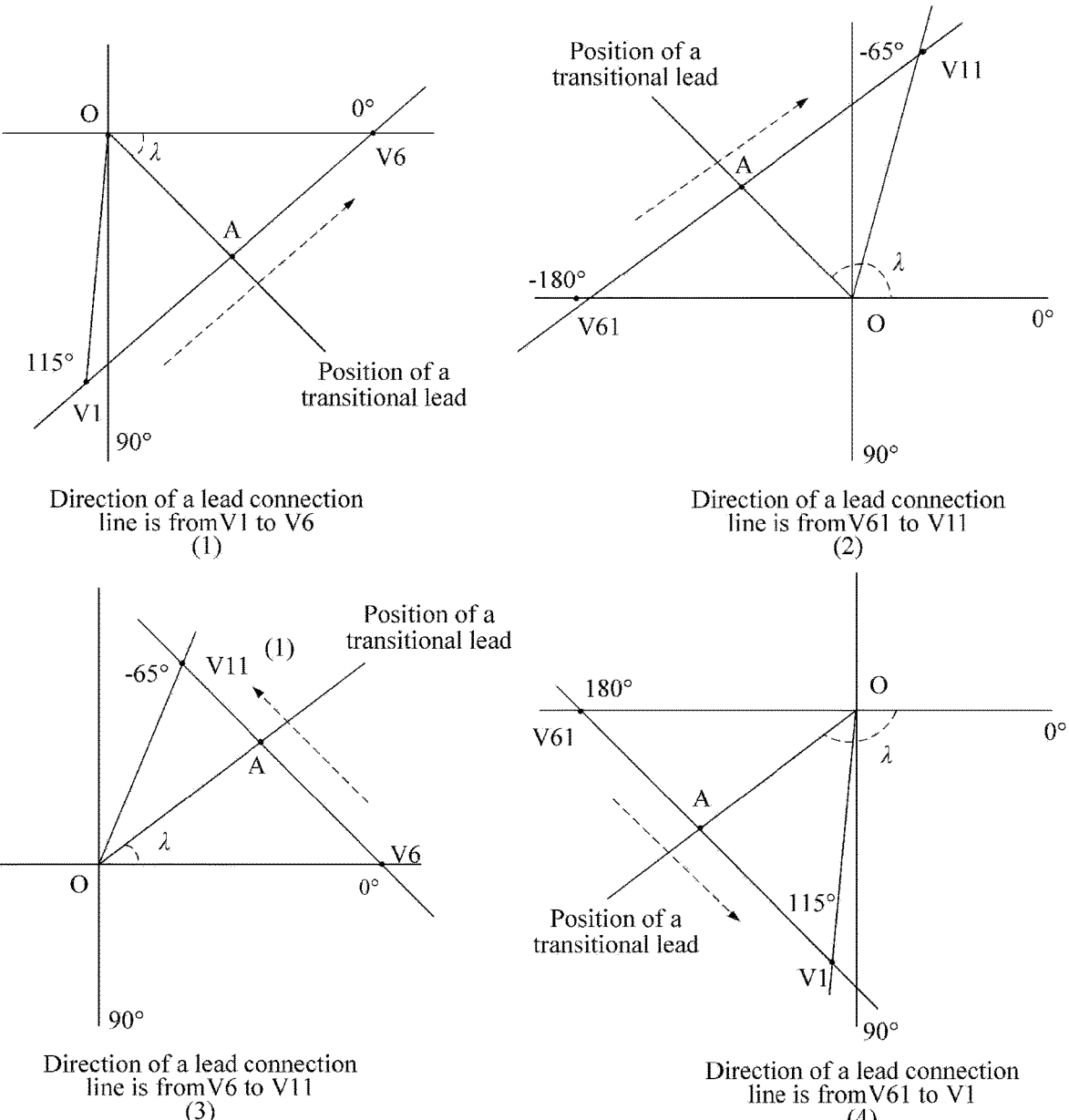
FIG. 8 is a schematic diagram of determining a position of a transitional lead according to a proportion in an embodiment.

The following clearly and completely describes the technical solutions in the embodiments of the present invention with reference to the accompanying drawings in the embodiments of the present invention. Clearly, the described embodiments are merely some rather than all of the embodiments of the present invention. Based on the embodiments of the present invention, all other embodiments obtained by a person of ordinary skill in the art without creative efforts fall within the protection scope of the present invention.

As shown in FIG. 1, an embodiment provides a method for determining a position of a transitional lead. An execution body of the method for determining a position of a transitional lead in this embodiment of the present invention is a device that can implement the method for determining a position of a transitional lead in this embodiment of the present invention. The device may include but is not limited to a mobile terminal and a server. The mobile terminal includes but is not limited to a mobile phone, a tablet, a smart watch, and a smart band, and the server includes but is not limited to a high-performance computer and a high-performance computer cluster. The method for determining a position of a transitional lead specifically includes the following steps:

Step 102: Obtain an R-wave amplitude corresponding to each of chest leads, where the chest leads include a V1 lead, a V2 lead, a V3 lead, a V4 lead, a V5 lead, and a V6 lead.

An electrocardiogram is a curve where a voltage changes with time. The electrocardiogram is recorded on a coordinate line, and a vertical coordinate indicates the voltage. For an upward wave, an amplitude is a distance from an upper edge of a baseline to a vertex, and for a downward wave, an amplitude is a distance from a lower edge of the baseline to a lower end, where the baseline is a line corresponding to a segment T-P.

In a QRS wave shown in FIG. 2, an R wave is an upward wave, and an S wave is a downward wave. Therefore, an R-wave amplitude is a distance from the peak of the R wave to the baseline, and is a positive value; and an S-wave amplitude is a distance from the valley of the S wave to the baseline, and is a negative value.

FIG. 3 shows orientations of chest leads on a transverse plane. It can be seen that a lead V1, a lead V2, a lead V3, a lead V4, a lead V5 and a lead V6 are in different positions. Angles corresponding to the lead V1, the lead V2, the lead V3, the lead V4, the lead V5 and the lead V6 are respectively 115°, 94°, 58°, 47°, 22°, and 0°.

Step 104: Obtain an S-wave amplitude corresponding to each chest lead.

Step 106: Determine a position of a transitional lead according to a sum of the R-wave amplitudes and the S-wave amplitudes corresponding to all the chest leads.

In this embodiment of the present invention, the sum of the R-wave amplitude and the S-wave amplitude is an algebraic sum of the R-wave amplitude and the S-wave amplitude. When a sum of an R-wave amplitude and an S-wave amplitude of a lead is a negative value, the lead is referred to as being in a negative direction. When a sum of an R-wave amplitude and an S-wave amplitude of a lead is a positive value, the lead is referred to as being in a positive direction.

As shown in FIG. 4, a transitional lead shaft has the following features: When a QRS ring is in a left rear position, a V1 lead is in a negative direction, a V6 lead is in a positive direction, and a transitional lead is in a left front position. When the QRS ring is in a right rear position, the lead V1 and the lead V6 are both in the negative direction, and the transitional lead is in the left rear position. When the QRS ring is in a right front position, the lead V1 is in the positive direction, the lead V6 is in the negative direction, and the transitional lead is in the right rear position. When the QRS ring is in a left front position (such as type A pre-excitation), the lead V1 and the lead V6 are both in the positive direction, and the transitional lead is in the right front position.

As shown in FIG. 5, step 106 of determining a position of a transitional lead according to a sum of the R-wave amplitudes and the S-wave amplitudes corresponding to all the chest leads includes: step 106A of obtaining a first amplitude sum by means of calculation according to an R-wave amplitude and an S-wave amplitude that are corresponding to the V1 lead; step 106B of obtaining a second amplitude sum by means of calculation according to an R-wave amplitude and an S-wave amplitude that are corresponding to the V2 lead; step 106C of obtaining a third amplitude sum by means of calculation according to an R-wave amplitude and an S-wave amplitude that are corresponding to the V3 lead; step 106D of obtaining a fourth amplitude sum by means of calculation according to an R-wave amplitude and an S-wave amplitude that are corresponding to the V4 lead; step 106E of obtaining a fifth amplitude sum by means of calculation according to an R-wave amplitude and an S-wave amplitude that are corresponding to the V5 lead; step 106F of obtaining a sixth amplitude sum by means of calculation according to an R-wave amplitude and an S-wave amplitude that are corresponding to the V6 lead; and step 106G of determining the position of the transitional lead according to the first amplitude sum, the second amplitude sum, the third amplitude sum, the fourth amplitude sum, the fifth amplitude sum, and the sixth amplitude sum.

For example, if the R-wave amplitude of the V1 lead is t1 and the S-wave amplitude thereof is t2, the sum of the R-wave amplitude and the S-wave amplitude is t1+t2, that is, the first amplitude sum is t1+t2.

Step 106G of determining the position of the transitional lead according to the first amplitude sum, the second amplitude sum, the third amplitude sum, the fourth amplitude sum, the fifth amplitude sum, and the sixth amplitude sum includes:

106G1. If the first amplitude sum, the second amplitude sum, the third amplitude sum, the fourth amplitude sum, the fifth amplitude sum, and the sixth amplitude sum comprise an amplitude sum whose value is 0, determine a target lead corresponding to the amplitude sum whose value is 0.

106G2. Determine a position corresponding to the target lead as the position of the transitional lead.

For example, if the first amplitude sum is 0.2+(−0.4), the second amplitude sum is 0.3+(−0.3), the third amplitude sum is 0.4+(−0.3), the fourth amplitude sum is 0.45+(−0.25), the fifth amplitude sum is 0.5+(−0.2), and the sixth amplitude sum is 0.55+(−0.15), the third amplitude sum is 0, and it is determined that a target lead corresponding to the third amplitude sum is the V3 lead. In addition, a position 58° corresponding to the V3 lead is determined as the position of the transitional lead shaft, so as to accurately position the transitional lead.

Step 106G of determining the position of the transitional lead according to the first amplitude sum, the second amplitude sum, the third amplitude sum, the fourth amplitude sum, the fifth amplitude sum, and the sixth amplitude sum comprises: step 106G3: If the first amplitude sum, the second amplitude sum, the third amplitude sum, the fourth amplitude sum, the fifth amplitude sum, and the sixth amplitude sum do not comprise an amplitude sum whose value is 0, determine the position of the transitional lead according to the first amplitude sum and the sixth amplitude sum.

If none of the six amplitude sums is 0, in this case, to accurately position the transitional lead, the position of the transitional lead needs to be determined according to the first amplitude sum and the sixth amplitude sum.

As shown in FIG. 6, step 106G3 of determining the position of the transitional lead according to the first amplitude sum and the sixth amplitude sum includes:

Step 106G31: Obtain a first angle corresponding to the V1 lead and a second angle corresponding to the V6 lead.

As shown in FIG. 3, the first angle corresponding to the V1 lead is 115°, and the second angle corresponding to the V6 lead is 0°.

Step 106G32: Compare a value of the first amplitude sum with 0 to obtain a first positive and negative result, and compare a value of the sixth amplitude sum with 0 to obtain a second positive and negative result.

Step 106G33: Determine the position of the transitional lead according to the first angle, the second angle, the first amplitude sum, the sixth amplitude sum, the first positive and negative result, and the second positive and negative result.

Generally, from the lead V1 to the lead V6, absolute values of the R-wave amplitudes gradually increase, and absolute values of the S-wave amplitudes gradually decrease. Therefore, values of amplitude sums corresponding to different angles are different. In this embodiment of the present invention, the following relationship between the amplitude sum (x) and the angle (y) is defined:

$$y=kx+\lambda.$$

Therefore, the position of the transitional lead may be solved according to the foregoing linear relationship.

As shown in FIG. 7, step 106G33 of determining the position of the transitional lead according to the first angle, the second angle, the first amplitude sum, the sixth amplitude sum, the first positive and negative result, and the second positive and negative result includes:

Step 106G331: If the first positive and negative result is that the first amplitude sum is less than 0, and the second positive and negative result is that the sixth amplitude sum is greater than 0, determine the position of the transitional lead according to the first angle, the second angle, the first amplitude sum, and the sixth amplitude.

In an embodiment, as shown in FIG. 4, the first amplitude sum is less than 0, which indicates a negative direction of the V1 lead, and the sixth amplitude sum is greater than 0, which indicates a positive direction of the V6 lead. In this case, the transitional lead is in a left front position, and the V1 lead and/or the V6 lead do not need to be phase-inverted, and the position of the transitional lead is directly determined according to the first angle, the second angle, the first amplitude sum, and the sixth amplitude sum. Specifically, the first angle (115°) and the first amplitude sum (assumed to be represented by a) are substituted into y=kx+λ. In addition, the second angle (0°) and the sixth amplitude sum (assumed to be represented by b) are substituted into y=kx+λ, to obtain:

$$115=ak+\lambda$$

$$0=bk+\lambda.$$

The position of the transitional lead is a position in which the sum of the R-wave amplitude and the S-wave amplitude is 0, that is, an angle corresponding to x being 0. Therefore, λ is solved, to obtain the position of the transitional lead.

It may be obtained by using the foregoing formula that $$\lambda = 115 - \frac{115a}{a-b}.$$

The foregoing is converted into an absolute value for representation to obtain:

$$\lambda = 115 - \frac{115|a|}{|a|+|b|}.$$

Therefore, the position of the transitional lead is $$115 - \frac{115|a|}{|a|+|b|}.$$

In an embodiment, as shown in FIG. 8, the position of the transitional lead is determined according to a proportional relationship between an angle and a length of a lead connection line (a connection line between the V1 lead and the V6 lead). When the first amplitude sum is less than 0 and the sixth amplitude sum is greater than 0, as shown in FIG. 8(1), a direction of the lead connection line is determined as a direction from V1 to V6. Therefore, it is determined that:

$$\angle V1OA \text{ is)}(115°-0°)\times|a|/(|a|+|b|).$$

Therefore, the position λ of the transitional lead is obtained as 115°−115°/(|a|+|b|).

Step 106G332: If the first positive and negative result is that the first amplitude sum is greater than 0, and the second positive and negative result is that the sixth amplitude sum is less than 0, obtain a third angle corresponding to the phase-inverted V1 lead, wherein the third angle is determined according to the first angle, obtain a fourth angle corresponding to the phase-inverted V6 lead, wherein the fourth angle is determined according to the second angle, and determine the position of the transitional lead according to the third angle, the fourth angle, the first amplitude sum, and the sixth amplitude sum.

As shown in FIG. 4, the first amplitude sum is greater than 0, which indicates that the V1 lead is in the positive direction, and the sixth amplitude sum is less than 0, which indicates that the V6 lead is in the negative direction. In this case, the transitional lead is in a right rear position, and the V1 lead and the V6 lead need to be phase-inverted. Assuming that (x, y) represents the amplitude sum (x) and the angle (y), the V1 lead before phase inversion is: (a, 115°); the V1 lead after phase inversion is: (−a, −65°); the V6 lead before phase inversion is (b, 0°); and the V6 lead after phase inversion is: (−b, −180°). Therefore, the third angle is −65°, the fourth angle is −180°. (−a, −65°) and (−b, −180°) are substituted into y=kx+λ, to obtain:

$$\lambda = \frac{115b}{b-a} - 180.$$

Because b is less than 0, and a is greater than 0, the foregoing is converted into an absolute value for representation to obtain:

$$\lambda = \frac{115|b|}{|b|+|a|} - 180.$$

Therefore, the position of the transitional lead is $$\frac{115|b|}{|b|+|a|} - 180.$$

In an embodiment, when the first amplitude sum is greater than 0, and the sixth amplitude sum is less than 0, the lead V1 and the lead V6 are phase-inverted, the phase-inverted lead V1 is corresponding to V11, and the phase-inverted lead V6 is corresponding to V61. Therefore, as shown in FIG. 8(2), the direction of the lead connection line is determined as a direction from V61 to V11, and then it is determined that:

$$\angle V61OA \text{ is)}(−65°−(−180°))\times|b|/(|a|+|b|).$$

Therefore, the position λ of the transitional lead is obtained as −180°±115°|b|/(|a|+|b|).

Step 106G333: If the first positive and negative result is that the first amplitude sum is less than 0, and the second positive and negative result is that the sixth amplitude sum is less than 0, obtain a third angle corresponding to the phase-inverted V1 lead, and determine the position of the transitional lead according to the third angle, the second angle, the first amplitude sum, and the sixth amplitude sum.

As shown in FIG. 4, the first amplitude sum is less than 0, which indicates that the V1 lead is in the negative direction, and the sixth amplitude sum is less than 0, which indicates that the V6 lead is in the negative direction. In this case, the transitional lead is in a left rear position, and the V1 lead needs to be phase-inverted. The phase-inverted V1 lead is: (−a, −65°). Therefore, the position of the transitional lead is determined according to (−a, −65°) and (b, 0°). (−a, −65°) and (b, 0°) are substituted into y=kx+λ, to obtain:

$$−65=−ak+\lambda$$

$$0=bk+\lambda.$$

It may be obtained by using the foregoing formula that $$k = \frac{65}{a+b},$$

$$\lambda = -\frac{65b}{a+b}.$$

The foregoing is converted into an absolute value for representation to obtain:

$$\lambda = -\frac{65|b|}{|a|+|b|}.$$

Therefore, the position of the transitional lead is $$-\frac{65|b|}{|a|+|b|}.$$

In an embodiment, when the first amplitude sum is less than 0, and the sixth amplitude sum is less than 0, the lead V1 is phase-inverted, and the lead V1 is corresponding to V11 after phase inversion. Therefore, as shown in FIG. 8(3), the direction of the lead connection line is determined as a direction from V6 to V11, and then the position λ of the transitional lead is determined as:

$$\lambda = \angle V6OA \text{ is } (-65°-0°) \times |b|/(|a|+|b|).$$

Step 106G334: If the first positive and negative result is that the first amplitude sum is greater than 0, and the second positive and negative result is that the sixth amplitude sum is greater than 0, obtain a fourth angle corresponding to the phase-inverted V6 lead, and determine the position of the transitional lead according to the first angle, the fourth angle, the first amplitude sum, and the sixth amplitude sum.

As shown in FIG. 4, the first amplitude sum is greater than 0, which indicates that the V1 lead is in the positive direction, and the sixth amplitude sum is greater than 0, which indicates that the V6 lead is in the positive direction. In this case, the transitional lead is in a right front position, and the V6 lead needs to be phase-inverted. The phase-inverted V6 lead is: $(-b, -180°)$. Therefor, the position of the transitional lead is determined according to $(a, 115°)$ and $(-b, 180°)$. $(a, 115°)$ and $(-b, 180°)$ are substituted into $y=kx+\lambda$, to obtain:

$$115 = ak + \lambda$$

$$180 = -bk + \lambda.$$

It may be obtained by using the foregoing formula that $$k = \frac{-65}{a+b},$$

$$\lambda = 180 - \frac{65b}{a+b}.$$

The foregoing is converted into an absolute value for representation to obtain:

$$\lambda = 180 - \frac{65|b|}{|a| + |b|}.$$

Therefore, the position of the transitional lead is $$180 - \frac{65|b|}{|a| + |b|}.$$

In an embodiment, when the first amplitude sum is greater than 0, and the sixth amplitude sum is greater than 0, the lead V6 is phase-inverted, and the phase-inverted lead V6 is corresponding to V61. Correspondingly, the angle of the phase-inverted lead V6 is 180°. Therefore, as shown in FIG. 8(4), the direction of the lead connection line is determined as a direction from V61 to V11, and then it is determined that:

$$\angle V61OA \text{ is } (115°-180°) \times |b|/(|a|+|b|).$$

Therefore, the position λ of the transitional lead is obtained as 180°−(65°|b|/(|a|+|b|)).

The foregoing method for determining a position of a transitional lead includes: first obtaining an R-wave amplitude corresponding to each of chest leads, where the chest leads include a V1 lead, a V2 lead, a V3 lead, a V4 lead, a V5 lead, and a V6 lead; then obtaining an S-wave amplitude corresponding to each chest lead; and finally determining a position of a transitional lead according to a sum of the R-wave amplitudes and the S-wave amplitudes corresponding to all the chest leads. It can be learned that, in the foregoing manner, compared with a manner in which a target lead shaft is determined by using a ratio of an R wave to an S wave, and then a position of the target lead shaft is determined as a position of a transitional lead shaft, this manner is capable of directly determining the position of the transitional lead, and has higher accuracy.

Figure 9:
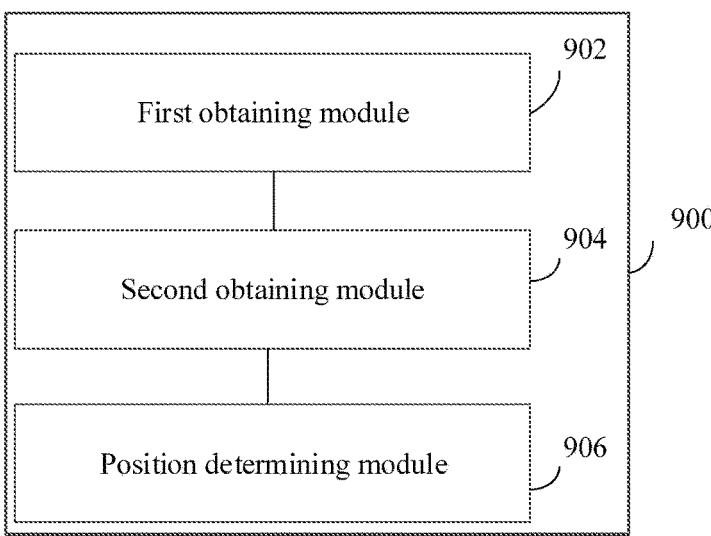
FIG. 9 is a structural block diagram of an apparatus for determining a position of a transitional lead according to an embodiment.

As shown in FIG. 9, an apparatus 900 for determining a position of a transitional lead is provided, specifically including:

a first obtaining module 902, configured to obtain an R-wave amplitude corresponding to each of chest leads, wherein the chest leads comprise a V1 lead, a V2 lead, a V3 lead, a V4 lead, a V5 lead, and a V6 lead;

a second obtaining module 904, configured to obtain an S-wave amplitude corresponding to each chest lead; and a position determining module 906, configured to determine a position of a transitional lead according to a sum of the R-wave amplitudes and the S-wave amplitudes corresponding to all the chest leads.

The foregoing apparatus for determining a position of a transitional lead first obtains an R-wave amplitude corresponding to each of chest leads, where the chest leads include a V1 lead, a V2 lead, a V3 lead, a V4 lead, a V5 lead, and a V6 lead; then obtains an S-wave amplitude corresponding to each chest lead; and finally determines a position of a transitional lead according to a sum of the R-wave amplitudes and the S-wave amplitudes corresponding to all the chest leads. It can be learned that, in the foregoing manner, compared with a manner in which a target lead shaft is determined by using a ratio of an R wave to an S wave, and then a position of the target lead shaft is determined as a position of a transitional lead shaft, this manner is capable of directly determining the position of the transitional lead, and has higher accuracy.

In an embodiment, the position determining module 906 includes: a first amplitude module, configured to obtain a first amplitude sum by means of calculation according to an R-wave amplitude and an S-wave amplitude that are corresponding to the V1 lead; a second amplitude module, configured to obtain a second amplitude sum by means of calculation according to an R-wave amplitude and an S-wave amplitude that are corresponding to the V2 lead; a third amplitude module, configured to obtain a third amplitude sum by means of calculation according to an R-wave amplitude and an S-wave amplitude that are corresponding to the V3 lead; a fourth amplitude module, configured to obtain a fourth amplitude sum by means of calculation according to an R-wave amplitude and an S-wave amplitude that are corresponding to the V4 lead; a fifth amplitude module, configured to obtain a fifth amplitude sum by means of calculation according to an R-wave amplitude and an S-wave amplitude that are corresponding to the V5 lead; a sixth amplitude module, configured to obtain a sixth amplitude sum by means of calculation according to an R-wave amplitude and an S-wave amplitude that are corresponding to the V6 lead; and an amplitude synthesis module, configured to determine the position of the transitional lead according to the first amplitude sum, the second amplitude sum, the third amplitude sum, the fourth amplitude sum, the fifth amplitude sum, and the sixth amplitude sum.

In an embodiment, the amplitude synthesis module includes: a 0-value amplitude module, configured to: if the first amplitude sum, the second amplitude sum, the third amplitude sum, the fourth amplitude sum, the fifth amplitude sum, and the sixth amplitude sum include an amplitude sum whose value is 0, determine a target lead corresponding to the amplitude sum whose value is 0; and a 0-value position module, configured to determine a position corresponding to the target lead as the position of the transitional lead.

In an embodiment, the amplitude synthesis module includes a non-0-value amplitude module configured to: if the first amplitude sum, the second amplitude sum, the third amplitude sum, the fourth amplitude sum, the fifth amplitude sum, and the sixth amplitude sum do not include an amplitude sum whose value is 0, determine the position of the transitional lead according to the first amplitude sum and the sixth amplitude sum.

In an embodiment, the non-0-value amplitude module includes: a first angle module, configured to obtain a first angle corresponding to the V1 lead and a second angle corresponding to the V6 lead; a second angle module, configured to compare a value of the first amplitude sum with 0 to obtain a first positive or negative result, and compare a value of the sixth amplitude sum with 0 to obtain a second positive or negative result; and an angle position module, configured to determine the position of the transitional lead according to the first angle, the second angle, the first amplitude sum, the sixth amplitude sum, the first positive or negative result, and the second positive or negative result.

In an embodiment, the angle position module includes: a first angle position module, configured to: if the first positive or negative result is that the first amplitude sum is less than 0, and the second positive or negative result is that the sixth amplitude sum is greater than 0, determine the position of the transitional lead according to the first angle, the second angle, the first amplitude sum, and the sixth amplitude; a second angle position module, configured to: if the first positive or negative result is that the first amplitude sum is greater than 0, and the second positive or negative result is that the sixth amplitude sum is less than 0, obtain a third angle corresponding to the phase-inverted V1 lead, where the third angle is determined according to the first angle, obtain a fourth angle corresponding to the phase-inverted V6 lead, where the fourth angle is determined according to the second angle, and determine the position of the transitional lead according to the third angle, the fourth angle, the first amplitude sum, and the sixth amplitude sum; a third angle position module, configured to: if the first positive or negative result is that the first amplitude sum is less than 0, and the second positive or negative result is that the sixth amplitude sum is less than 0, obtain a third angle corresponding to the phase-inverted V1 lead, and determine the position of the transitional lead according to the third angle, the second angle, the first amplitude sum, and the sixth amplitude sum; and a fourth angle position module, configured to: if the first positive or negative result is that the first amplitude sum is greater than 0, and the second positive or negative result is that the sixth amplitude sum is greater than 0, obtain a fourth angle corresponding to the phase-inverted V6 lead, and determine the position of the transitional lead according to the first angle, the fourth angle, the first amplitude sum, and the sixth amplitude sum.

Figure 10:
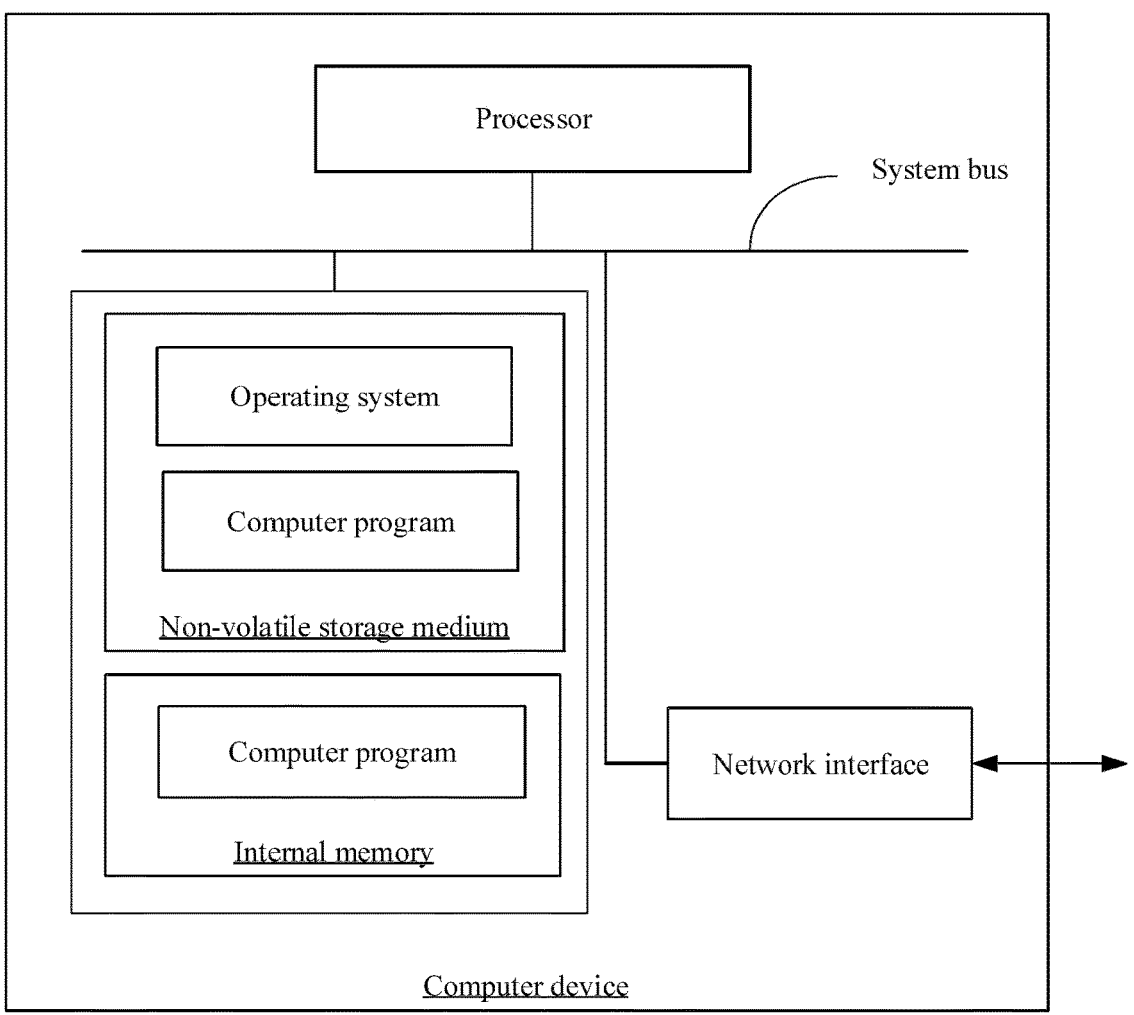
FIG. 10 is a structural block diagram of a computer device according to an embodiment.

FIG. 10 is an internal structure diagram of a computer device in an embodiment. The computer device may be specifically a digital pathological section scanner. As shown in FIG. 10, the computer device includes a processor, a memory, and a network interface that are connected by using a system bus. The memory includes a non-volatile storage medium and an internal memory. The non-volatile storage medium of the computer device stores an operating system, and may further store a computer program. When the computer program is executed by the processor, the processor may implement a method for determining a position of a transitional lead. The internal memory may also store a computer program. When the computer program is executed by the processor, the processor may perform a method for determining a position of a transitional lead. A person skilled in the art may understand that the structure shown in FIG. 10 is merely a block diagram of a partial structure related to the solutions of this application, and does not constitute a limitation on a computer device to which the solutions of this application are applied. A specific computer device may include more or fewer components than those shown in the figure, or combine some components, or have different component arrangements.

In an embodiment, the method for determining a position of a transitional lead provided in this application may be implemented in a form of a computer program, and the computer program may run on the computer device shown in FIG. 10. The memory of the computer device may store program templates constituting the apparatus for determining a position of a transitional lead, for example, the first obtaining module 902, the second obtaining module 904, and the position determining module 906.

A computer device includes a memory and a processor, where the memory stores a computer program, and when the computer program is executed by the processor, the processor performs the following steps:

obtaining an R-wave amplitude corresponding to each of chest leads, where the chest leads include a V1 lead, a V2 lead, a V3 lead, a V4 lead, a V5 lead, and a V6 lead;

obtaining an S-wave amplitude corresponding to each chest lead; and determining a position of a transitional lead according to a sum of the R-wave amplitudes and the S-wave amplitudes corresponding to all the chest leads.

The foregoing computer device first obtains an R-wave amplitude corresponding to each of chest leads, where the chest leads include a V1 lead, a V2 lead, a V3 lead, a V4 lead, a V5 lead, and a V6 lead; then obtains an S-wave amplitude corresponding to each chest lead; and finally determines a position of a transitional lead according to a sum of the R-wave amplitudes and the S-wave amplitudes corresponding to all the chest leads. It can be learned that, in the foregoing manner, compared with a manner in which a target lead shaft is determined by using a ratio of an R wave to an S wave, and then a position of the target lead shaft is determined as a position of a transitional lead shaft, this manner is capable of directly determining the position of the transitional lead, and has higher accuracy.

In an embodiment, the determining a position of a transitional lead according to a sum of the R-wave amplitudes and the S-wave amplitudes corresponding to all the chest leads includes: obtaining a first amplitude sum by means of calculation according to an R-wave amplitude and an S-wave amplitude that are corresponding to the V1 lead; obtaining a second amplitude sum by means of calculation according to an R-wave amplitude and an S-wave amplitude that are corresponding to the V2 lead; obtaining a third amplitude sum by means of calculation according to an R-wave amplitude and an S-wave amplitude that are corresponding to the V3 lead; obtaining a fourth amplitude sum by means of calculation according to an R-wave amplitude and an S-wave amplitude that are corresponding to the V4 lead; obtaining a fifth amplitude sum by means of calculation according to an R-wave amplitude and an S-wave amplitude that are corresponding to the V5 lead; obtaining a sixth amplitude sum by means of calculation according to an R-wave amplitude and an S-wave amplitude that are corresponding to the V6 lead; and determining the position of the transitional lead according to the first amplitude sum, the second amplitude sum, the third amplitude sum, the fourth amplitude sum, the fifth amplitude sum, and the sixth amplitude sum.

In an embodiment, the determining the position of the transitional lead according to the first amplitude sum, the second amplitude sum, the third amplitude sum, the fourth amplitude sum, the fifth amplitude sum, and the sixth amplitude sum includes: if the first amplitude sum, the second amplitude sum, the third amplitude sum, the fourth amplitude sum, the fifth amplitude sum, and the sixth amplitude sum include an amplitude sum whose value is 0, determining a target lead corresponding to the amplitude sum whose value is 0; and determining a position corresponding to the target lead as the position of the transitional lead.

In an embodiment, the determining the position of the transitional lead according to the first amplitude sum, the second amplitude sum, the third amplitude sum, the fourth amplitude sum, the fifth amplitude sum, and the sixth amplitude sum includes: if the first amplitude sum, the second amplitude sum, the third amplitude sum, the fourth amplitude sum, the fifth amplitude sum, and the sixth amplitude sum do not include an amplitude sum whose value is 0, determining the position of the transitional lead according to the first amplitude sum and the sixth amplitude sum.

In an embodiment, the determining the position of the transitional lead according to the first amplitude sum and the sixth amplitude sum includes: obtaining a first angle corresponding to the V1 lead and a second angle corresponding to the V6 lead; comparing a value of the first amplitude sum with 0 to obtain a first positive or negative result, and comparing a value of the sixth amplitude sum with 0 to obtain a second positive or negative result; and determining the position of the transitional lead according to the first angle, the second angle, the first amplitude sum, the sixth amplitude sum, the first positive or negative result, and the second positive or negative result.

In an embodiment, the determining the position of the transitional lead according to the first angle, the second angle, the first amplitude sum, the sixth amplitude sum, the first positive or negative result, and the second positive or negative result includes: if the first positive or negative result is that the first amplitude sum is less than 0, and the second positive or negative result is that the sixth amplitude sum is greater than 0, determining the position of the transitional lead according to the first angle, the second angle, the first amplitude sum, and the sixth amplitude; or if the first positive or negative result is that the first amplitude sum is greater than 0, and the second positive or negative result is that the sixth amplitude sum is less than 0, obtaining a third angle corresponding to the phase-inverted V1 lead, where the third angle is determined according to the first angle, obtaining a fourth angle corresponding to the phase-inverted V6 lead, where the fourth angle is determined according to the second angle, and determining the position of the transitional lead according to the third angle, the fourth angle, the first amplitude sum, and the sixth amplitude sum; or if the first positive or negative result is that the first amplitude sum is less than 0, and the second positive or negative result is that the sixth amplitude sum is less than 0, obtaining a third angle corresponding to the phase-inverted V1 lead, and determining the position of the transitional lead according to the third angle, the second angle, the first amplitude sum, and the sixth amplitude sum; or if the first positive or negative result is that the first amplitude sum is greater than 0, and the second positive or negative result is that the sixth amplitude sum is greater than 0, obtaining a fourth angle corresponding to the phase-inverted V6 lead, and determining the position of the transitional lead according to the first angle, the fourth angle, the first amplitude sum, and the sixth amplitude sum.

In an embodiment, a computer readable storage medium is provided, and stores a computer program. When the computer program is executed by a processor, the processor performs the following steps:

obtaining an R-wave amplitude corresponding to each of chest leads, where the chest leads include a V1 lead, a V2 lead, a V3 lead, a V4 lead, a V5 lead, and a V6 lead;

obtaining an S-wave amplitude corresponding to each chest lead; and determining a position of a transitional lead according to a sum of the R-wave amplitudes and the S-wave amplitudes corresponding to all the chest leads.

The foregoing computer readable storage medium first obtains an R-wave amplitude corresponding to each of chest leads, where the chest leads include a V1 lead, a V2 lead, a V3 lead, a V4 lead, a V5 lead, and a V6 lead; then obtains an S-wave amplitude corresponding to each chest lead; and finally determines a position of a transitional lead according to a sum of the R-wave amplitudes and the S-wave amplitudes corresponding to all the chest leads. It can be learned that, in the foregoing manner, compared with a manner in which a target lead shaft is determined by using a ratio of an R wave to an S wave, and then a position of the target lead shaft is determined as a position of a transitional lead shaft, this manner is capable of directly determining the position of the transitional lead, and has higher accuracy.

In an embodiment, the determining a position of a transitional lead according to a sum of the R-wave amplitudes and the S-wave amplitudes corresponding to all the chest leads includes: obtaining a first amplitude sum by means of calculation according to an R-wave amplitude and an S-wave amplitude that are corresponding to the V1 lead; obtaining a second amplitude sum by means of calculation according to an R-wave amplitude and an S-wave amplitude that are corresponding to the V2 lead; obtaining a third amplitude sum by means of calculation according to an R-wave amplitude and an S-wave amplitude that are corresponding to the V3 lead; obtaining a fourth amplitude sum by means of calculation according to an R-wave amplitude and an S-wave amplitude that are corresponding to the V4 lead; obtaining a fifth amplitude sum by means of calculation according to an R-wave amplitude and an S-wave amplitude that are corresponding to the V5 lead; obtaining a sixth amplitude sum by means of calculation according to an R-wave amplitude and an S-wave amplitude that are corresponding to the V6 lead; and determining the position of the transitional lead according to the first amplitude sum, the second amplitude sum, the third amplitude sum, the fourth amplitude sum, the fifth amplitude sum, and the sixth amplitude sum.

In an embodiment, the determining the position of the transitional lead according to the first amplitude sum, the second amplitude sum, the third amplitude sum, the fourth amplitude sum, the fifth amplitude sum, and the sixth amplitude sum includes: if the first amplitude sum, the second amplitude sum, the third amplitude sum, the fourth amplitude sum, the fifth amplitude sum, and the sixth amplitude sum include an amplitude sum whose value is 0, determining a target lead corresponding to the amplitude sum whose value is 0; and determining a position corresponding to the target lead as the position of the transitional lead.

In an embodiment, the determining the position of the transitional lead according to the first amplitude sum, the second amplitude sum, the third amplitude sum, the fourth amplitude sum, the fifth amplitude sum, and the sixth amplitude sum includes: if the first amplitude sum, the second amplitude sum, the third amplitude sum, the fourth amplitude sum, the fifth amplitude sum, and the sixth amplitude sum do not include an amplitude sum whose value is 0, determining the position of the transitional lead according to the first amplitude sum and the sixth amplitude sum.

In an embodiment, the determining the position of the transitional lead according to the first amplitude sum and the sixth amplitude sum includes: obtaining a first angle corresponding to the V1 lead and a second angle corresponding to the V6 lead; comparing a value of the first amplitude sum with 0 to obtain a first positive or negative result, and comparing a value of the sixth amplitude sum with 0 to obtain a second positive or negative result; and determining the position of the transitional lead according to the first angle, the second angle, the first amplitude sum, the sixth amplitude sum, the first positive or negative result, and the second positive or negative result.

In an embodiment, the determining the position of the transitional lead according to the first angle, the second angle, the first amplitude sum, the sixth amplitude sum, the first positive or negative result, and the second positive or negative result includes: if the first positive or negative result is that the first amplitude sum is less than 0, and the second positive or negative result is that the sixth amplitude sum is greater than 0, determining the position of the transitional lead according to the first angle, the second angle, the first amplitude sum, and the sixth amplitude; or if the first positive or negative result is that the first amplitude sum is greater than 0, and the second positive or negative result is that the sixth amplitude sum is less than 0, obtaining a third angle corresponding to the phase-inverted V1 lead, where the third angle is determined according to the first angle, obtaining a fourth angle corresponding to the phase-inverted V6 lead, where the fourth angle is determined according to the second angle, and determining the position of the transitional lead according to the third angle, the fourth angle, the first amplitude sum, and the sixth amplitude sum; or if the first positive or negative result is that the first amplitude sum is less than 0, and the second positive or negative result is that the sixth amplitude sum is less than 0, obtaining a third angle corresponding to the phase-inverted V1 lead, and determining the position of the transitional lead according to the third angle, the second angle, the first amplitude sum, and the sixth amplitude sum; or if the first positive or negative result is that the first amplitude sum is greater than 0, and the second positive or negative result is that the sixth amplitude sum is greater than 0, obtaining a fourth angle corresponding to the phase-inverted V6 lead, and determining the position of the transitional lead according to the first angle, the fourth angle, the first amplitude sum, and the sixth amplitude sum.

It should be noted that the foregoing method for determining a position of a transitional lead, the apparatus for determining a position of a transitional lead, the computer device, and the computer readable storage medium belong to a general inventive concept, and the content in the embodiments of the method for determining a position of a transitional lead, the apparatus for determining a position of a transitional lead, the computer device, and the computer readable storage medium may be mutually applied.

A person of ordinary skill in the art may understand that all or some of the processes in the methods in the foregoing embodiments may be implemented by a computer program instructing related hardware. The program may be stored in a non-volatile computer readable storage medium. When the program is executed, the processes in the foregoing method embodiments may be included. Any reference to a memory, a storage, a database, or another medium used in the embodiments provided in this application may include a non-volatile and/or volatile memory. The non-volatile memory may include a read-only memory (ROM), a programmable ROM (PROM), an electrically programmable ROM (EPROM), an electrically erasable programmable ROM (EEPROM), or a flash memory. The volatile memory may include a random access memory (RAM) or an external cache memory. As an illustration and not a limitation, the RAM may be obtained in multiple forms, such as static RAM (SRAM), dynamic RAM (DRAM), synchronous DRAM (SDRAM), dual data rate SDRAM (DDRSDRAM), enhanced SDRAM (ESDRAM), synchronous link (Synchlink) DRAM (SLDRAM), Rambus (Rambus) direct RAM (RDRAM), direct Rambus dynamic RAM (DRDRAM), and Rambus dynamic RAM (RDRAM).

The technical features in the foregoing embodiments may be combined randomly. To make the description brief, not all possible combinations of the technical features in the foregoing embodiments are described. However, as long as there is no contradiction between the combinations of the technical features, the combinations of the technical features should be considered to fall within the scope described in this specification.

The foregoing embodiments represent only several implementations of this application, and description thereof is relatively specific and detailed, but may not be construed as a limitation on the scope of this application. It should be noted that a person of ordinary skill in the art may make some modifications and improvements without departing from the concept of this application, which fall within the protection scope of this application. Therefore, the protection scope of the present application shall be subject to the appended claims.

What is claimed is:

1. A method for determining a position of a transitional lead, comprising:

obtaining an R-wave amplitude corresponding to each of chest leads, wherein the chest leads comprise a V1 lead, a V2 lead, a V3 lead, a V4 lead, a V5 lead, and a V6 lead;

obtaining an S-wave amplitude corresponding to each chest lead; and determining the position of the transitional lead according to a sum of the R-wave amplitudes and the S-wave amplitudes corresponding to all the chest leads, wherein the determining the position of the transitional lead according to the sum of the R-wave amplitudes and the S-wave amplitudes corresponding to all the chest leads comprises:

obtaining a first amplitude sum by means of calculation according to an R-wave amplitude and an S-wave amplitude that are corresponding to the V1 lead;

obtaining a second amplitude sum by means of calcula-
tion according to an R-wave amplitude and an S-wave
amplitude that are corresponding to the V2 lead;
obtaining a third amplitude sum by means of calculation
according to an R-wave amplitude and an S-wave
amplitude that are corresponding to the V3 lead;
obtaining a fourth amplitude sum by means of calculation
according to an R-wave amplitude and an S-wave
amplitude that are corresponding to the V4 lead;
obtaining a fifth amplitude sum by means of calculation
according to an R-wave amplitude and an S-wave
amplitude that are corresponding to the V5 lead;
obtaining a sixth amplitude sum by means of calculation
according to an R-wave amplitude and an S-wave
amplitude that are corresponding to the V6 lead; and
determining the position of the transitional lead according
to the first amplitude sum, the second amplitude sum,
the third amplitude sum, the fourth amplitude sum, the
fifth amplitude sum, and the sixth amplitude sum.

2. The method according to claim 1, wherein the deter-
mining the position of the transitional lead according to the
first amplitude sum, the second amplitude sum, the third
amplitude sum, the fourth amplitude sum, the fifth amplitude
sum, and the sixth amplitude sum comprises:
if the first amplitude sum, the second amplitude sum, the
third amplitude sum, the fourth amplitude sum, the fifth
amplitude sum, and the sixth amplitude sum comprise
an amplitude sum whose value is 0, determining a
target lead corresponding to the amplitude sum whose
value is 0; and
determining a position corresponding to the target lead as
the position of the transitional lead.

3. The method according to claim 1, wherein the deter-
mining the position of the transitional lead according to the
first amplitude sum, the second amplitude sum, the third
amplitude sum, the fourth amplitude sum, the fifth amplitude
sum, and the sixth amplitude sum comprises:
if the first amplitude sum, the second amplitude sum, the
third amplitude sum, the fourth amplitude sum, the fifth
amplitude sum, and the sixth amplitude sum do not
comprise an amplitude sum whose value is 0, deter-
mining the position of the transitional lead according to
the first amplitude sum and the sixth amplitude sum.

4. The method according to claim 3, wherein the deter-
mining the position of the transitional lead according to the
first amplitude sum and the sixth amplitude sum comprises:
obtaining a first angle corresponding to the V1 lead and a
second angle corresponding to the V6 lead;
comparing a value of the first amplitude sum with 0 to
obtain a first positive or negative result, and comparing
a value of the sixth amplitude sum with 0 to obtain a
second positive or negative result; and
determining the position of the transitional lead according
to the first angle, the second angle, the first amplitude
sum, the sixth amplitude sum, the first positive or
negative result, and the second positive or negative
result.

5. The method according to claim 4, wherein the deter-
mining the position of the transitional lead according to the
first angle, the second angle, the first amplitude sum, the
sixth amplitude sum, the first positive or negative result, and
the second positive or negative result comprises one of the
followings:
if the first positive or negative result is that the first
amplitude sum is less than 0, and the second positive or
negative result is that the sixth amplitude sum is greater
than 0, determining the position of the transitional lead according to the first angle, the second angle, the first
amplitude sum, and the sixth amplitude; if the first
positive or negative result is that the first amplitude
sum is greater than 0, and the second positive or
negative result is that the sixth amplitude sum is less
than 0, obtaining a third angle corresponding to the
phase-inverted V1 lead, wherein the third angle is
determined according to the first angle, obtaining a
fourth angle corresponding to the phase-inverted V6
lead, wherein the fourth angle is determined according
to the second angle, and determining the position of the
transitional lead according to the third angle, the fourth
angle, the first amplitude sum, and the sixth amplitude
sum;
if the first positive or negative result is that the first
amplitude sum is less than 0, and the second positive or
negative result is that the sixth amplitude sum is less
than 0, obtaining a third angle corresponding to the
phase-inverted V1 lead, and determining the position of
the transitional lead according to the third angle, the
second angle, the first amplitude sum, and the sixth
amplitude sum; and
if the first positive or negative result is that the first
amplitude sum is greater than 0, and the second positive
or negative result is that the sixth amplitude sum is
greater than 0, obtaining a fourth angle corresponding
to the phase-inverted V6 lead, and determining the
position of the transitional lead according to the first
angle, the fourth angle, the first amplitude sum, and the
sixth amplitude sum.

6. An apparatus for determining a position of a transitional
lead, comprising:
a first obtaining module, configured to obtain an R-wave
amplitude corresponding to each of chest leads,
wherein the chest leads comprise a V1 lead, a V2 lead,
a V3 lead, a V4 lead, a V5 lead, and a V6 lead;
a second obtaining module, configured to obtain an
S-wave amplitude corresponding to each chest lead;
and
a position determining module, configured to determine
the position of the transitional lead according to a sum
of the R-wave amplitudes and the S-wave amplitudes
corresponding to all the chest leads,
wherein the position determining module comprises:
a first amplitude module, configured to obtain a first
amplitude sum by means of calculation according to an
R-wave amplitude and an S-wave amplitude that are
corresponding to the V1 lead;
a second amplitude module, configured to obtain a second
amplitude sum by means of calculation according to an
R-wave amplitude and an S-wave amplitude that are
corresponding to the V2 lead;
a third amplitude module, configured to obtain a third
amplitude sum by means of calculation according to an
R-wave amplitude and an S-wave amplitude that are
corresponding to the V3 lead;
a fourth amplitude module, configured to obtain a fourth
amplitude sum by means of calculation according to an
R-wave amplitude and an S-wave amplitude that are
corresponding to the V4 lead;
a fifth amplitude module, configured to obtain a fifth
amplitude sum by means of calculation according to an
R-wave amplitude and an S-wave amplitude that are
corresponding to the V5 lead;
a sixth amplitude module, configured to obtain a sixth
amplitude sum by means of calculation according to an R-wave amplitude and an S-wave amplitude that are corresponding to the V6 lead; and an amplitude synthesis module, configured to determine the position of the transitional lead according to the first amplitude sum, the second amplitude sum, the third amplitude sum, the fourth amplitude sum, the fifth amplitude sum, and the sixth amplitude sum.

7. A computer device, comprising a memory, a processor, and a computer program stored in the memory and capable of running on the processor, wherein the processor implements the steps of the method for determining a position of a transitional lead according to claim 1 when executing the computer program.

8. A computer device, comprising a memory, a processor, and a computer program stored in the memory and capable of running on the processor, wherein the processor implements the steps of the method for determining a position of a transitional lead according to claim 2 when executing the computer program.

9. A computer device, comprising a memory, a processor, and a computer program stored in the memory and capable of running on the processor, wherein the processor implements the steps of the method for determining a position of a transitional lead according to claim 3 when executing the computer program.

10. A computer device, comprising a memory, a processor, and a computer program stored in the memory and capable of running on the processor, wherein the processor implements the steps of the method for determining a position of a transitional lead according to claim 4 when executing the computer program.

11. A computer device, comprising a memory, a processor, and a computer program stored in the memory and capable of running on the processor, wherein the processor implements the steps of the method for determining a position of a transitional lead according to claim 5 when executing the computer program.

12. A computer readable storage medium, wherein the computer readable storage medium stores a computer program, and the computer program is executed by a processor to implement the steps of the method for determining a position of a transitional lead according to claim 1.

13. A computer readable storage medium, wherein the computer readable storage medium stores a computer program, and the computer program is executed by a processor to implement the steps of the method for determining a position of a transitional lead according to claim 2.

14. A computer readable storage medium, wherein the computer readable storage medium stores a computer program, and the computer program is executed by a processor to implement the steps of the method for determining a position of a transitional lead according to claim 3.

15. A computer readable storage medium, wherein the computer readable storage medium stores a computer program, and the computer program is executed by a processor to implement the steps of the method for determining a position of a transitional lead according to claim 4.

16. A computer readable storage medium, wherein the computer readable storage medium stores a computer program, and the computer program is executed by a processor to implement the steps of the method for determining a position of a transitional lead according to claim 5.

* * * * *